(12) United States Patent
Farazi et al.

(10) Patent No.: US 7,620,448 B1
(45) Date of Patent: Nov. 17, 2009

(54) METHODS AND DEVICES FOR MONITORING MYOCARDIAL MECHANICAL STABILITY

(75) Inventors: Taraneh Ghaffari Farazi, San Jose, CA (US); Euljoon Park, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 488 days.

(21) Appl. No.: 11/421,915

(22) Filed: Jun. 2, 2006

(51) Int. Cl.
*A61B 5/04* (2006.01)

(52) U.S. Cl. .................................................... 600/515
(58) Field of Classification Search ......... 600/508–519; 607/9
See application file for complete search history.

(56) References Cited

U.S. PATENT DOCUMENTS

| | | | |
|---|---|---|---|
| 5,921,940 A | 7/1999 | Verrier | |
| 6,169,919 B1 | 1/2001 | Nearing | |
| 6,249,705 B1 | 6/2001 | Snell | |
| 6,497,655 B1 | 12/2002 | Linberg et al. | |
| 6,659,947 B1 | 12/2003 | Carter et al. | |
| 6,878,112 B2 | 4/2005 | Linberg et al. | |
| 6,915,156 B2 | 7/2005 | Christini | |
| 6,915,157 B2 | 7/2005 | Bennett | |
| 2002/0123673 A1 | 9/2002 | Webb et al. | |
| 2003/0041866 A1 | 3/2003 | Linberg et al. | |
| 2004/0002743 A1* | 1/2004 | Park et al. ................ | 607/25 |
| 2004/0109429 A1 | 6/2004 | Carter et al. | |
| 2004/0170154 A1 | 9/2004 | Carter et al. | |
| 2005/0004608 A1 | 1/2005 | Bullinga | |
| 2005/0010124 A1 | 1/2005 | Couderc | |
| 2005/0159787 A1 | 7/2005 | Linberg et al. | |

FOREIGN PATENT DOCUMENTS

| | | |
|---|---|---|
| WO | 0143823 | 6/2001 |
| WO | 0213686 | 2/2002 |
| WO | WO 2004062486 A2 | 7/2004 |
| WO | WO 2004062486 A3 | 7/2004 |

OTHER PUBLICATIONS

Non-Final Office Action mailed Jan. 23, 2009: Related U.S. Appl. No. 11/354,629.
Non-Final Office Action mailed Aug. 5, 2009: Related U.S. Appl. No. 11/354,629.
Bullinga et al., "Resonant Pacing Improves T-wave Alternans Testing in Patients with Dilated Cardiomyopathy" Heart Rhythm v1:S129, 2004.
Narayan et al. "Demonstration of the Proarrhythmic Preconditioning of Single Premature Extrastimuli by Use of the Magnitude, Phase and Distribution of Repolarization Alternans", Circulation. 1999; 100: 1887-1893.

* cited by examiner

*Primary Examiner*—Carl H Layno
*Assistant Examiner*—Roland Dinga
(74) *Attorney, Agent, or Firm*—Steven M. Mitchell

(57) ABSTRACT

Embodiments of the present invention relate to implantable systems, and methods for use therewith, for monitoring myocardial mechanical stability based on a signal that is indicative of mechanical functioning of a patient's heart for a plurality of consecutive beats. Certain embodiments use time domain techniques, while other embodiments use frequency domain techniques, to monitor myocardial mechanical stability. In certain embodiments the patient's heart is paced using a patterned pacing sequence that repeats every N beats. In other embodiments, the patient's heart need not be paced. This abstract is not intended to be a complete description of, or limit the scope of, the invention.

16 Claims, 12 Drawing Sheets

METHODS AND DEVICES FOR MONITORING MYOCARDIAL MECHANICAL STABILITY

CROSS REFERENCE TO RELATED APPLICATIONS

The present application relates to the following patent applications, which are incorporated herein by reference: U.S. patent application Ser. No. 11/354,629, entitled "Time Domain Monitoring of Myocardial Electrical Stability," filed Feb. 14, 2006; and U.S. patent application Ser. No. 11/354,732, entitled "Frequency Domain Monitoring of Myocardial Electrical Stability," filed Feb. 14, 2006.

FIELD OF THE INVENTION

The present invention generally relates methods and devices that are capable of monitoring myocardial mechanical stability, including detecting mechanical alternans patterns.

BACKGROUND

Mechanical alternans, also known as mechanical pulse alternans (MPA), relate to the situation where alternating contractions of the heart exhibit alternating values of contraction force or magnitude that cause ejected blood to exhibit similar alternating values of diastolic pressure amplitude. More specifically, the presence of mechanical alternans can be defined by a consistent alternation in peak left ventricular (LV) pressure, or dP/dt, in successive beats.

Visible mechanical alternans have been observed in patients with severe congestive heart failure caused by global left ventricular dysfunction, and is considered to be a terminal sign in this population. Mechanical alternans is characterized by alternating strong and weak beats with a substantially constant beat-to-beat interval. Although its precise origin remains unclear, studies have suggested a link to abnormal intracellular Ca2+ cycling in failing cardiomyocytes. Studies have also shown that prevalence of mechanical alternans increases with exercise and dobutamine loading compared to rest, indicating that mechanical alternan is a rate dependent phenomenon. Accordingly, it is believed that it would be useful to provide methods and systems for chronically monitoring for mechanical alternans, and more generally, monitoring myocardial electrical stability.

BRIEF SUMMARY OF THE INVENTION

Embodiments of the present invention relate to implantable systems, and methods for use therewith, for monitoring myocardial mechanical stability. In accordance with an embodiment, a signal is obtained that is indicative of mechanical functioning of the patient's heart for a plurality of consecutive beats, and a metric of the signal is determined for each of the plurality of consecutive beats. The signal that is indicative of the mechanical function of the patient's heart can be obtained using one or more implanted sensor. In one embodiment, the sensor is a pressure transducer that obtains measures of ventricular pressure. In another embodiment, the sensor is an accelerometer that obtains measures of contraction strength. In a further embodiment, the sensor is a blood flow transducer that obtains measures of blood flow rate. In still another embodiment, the sensor is an acoustic transducer that obtains measures of heart sounds. Such an acoustic transducer can be, e.g., a microphone or an accelerometer that responds to acoustic vibrations transmitted through body fluids, to thereby detect alternating loud and soft sounds. In a further embodiment, the sensor is an impedance measuring circuit having voltage sense electrodes to measure volumetric alternans, which is a surrogate of mechanical alternans. In still another embodiment, the sensor is a photo-plethysmography (PPG) sensor. In a further embodiment, the sensor is an SVO2 sensor. These are just some examples of sensors that are capable of measuring the mechanical functioning of the heart, or a surrogate thereof, in accordance with embodiments of the present invention. Other types of sensors capable of measuring the mechanical functioning of the heart, or a surrogate thereof, are also within the scope of the present invention.

The plurality of consecutive beats is divided into a plurality of sets of N consecutive beats, wherein N is an integer that is at least 2. In specific embodiments, N is an integer that is at least 3. Then, for each of the plurality of sets of N consecutive beats, one or more pairwise combination of the metrics is determined for consecutive pairs of beats. Corresponding pairwise combinations, determined for the plurality of sets of N consecutive beats, are cumulative averaged or cumulative summed to thereby produce a plurality of cumulative values. Myocardial mechanical stability is monitored based on the cumulative values, e.g., by determining whether mechanical alternans are present. In accordance with a specific embodiment, myocardial mechanical stability is tracked by repeating the above steps over time.

In accordance with an embodiment, the patient's heart is paced for a period of time using a patterned pacing sequence that repeats every N beats, and the signal indicative of mechanical functioning of the patient's heart is obtained while the patient's heart is being paced using the patterned pacing sequence.

In accordance with an embodiment, corresponding pairwise differences are cumulative averaged to produce the plurality of cumulative values, and mechanical alternans are determined to be present when the cumulative values exceed a specified threshold.

In accordance with another embodiment, corresponding pairwise differences are cumulative summed to produce the plurality of cumulative values, and mechanical alternans are determined to be present when a slope of the cumulative values exceeds a specified slope threshold.

In accordance with an embodiment, the pairwise combinations are bounded prior to the cumulative averaging or cumulative summing.

In accordance with certain embodiments, disruptive beats are detected, if they exist, based on the cumulative values. This way the disruptive beats can be compensated for. In a specific embodiment, where corresponding pairwise differences are cumulative summed to determine the plurality of cumulative values, a disruptive beat is detected if the cumulative values continually stay within a range and then suddenly go outside the range and continually stay within a further range. In another embodiment, where corresponding pairwise differences are cumulative summed to produce the plurality of cumulative values, a disruptive beat is detected if the cumulative values continually increase and then suddenly continually decrease.

The above described embodiments relate to monitoring myocardial mechanical stability using time domain data and time domain techniques. Further embodiments, summarized below, convert time domain data to frequency domain data, so that frequency domain techniques can be used for monitoring myocardial mechanical stability.

In accordance with specific embodiments of the present invention, an N beat alternans pattern can be detected from a signal that is indicative of mechanical functioning of the patient's heart for a plurality of consecutive beats, where N is an integer that is at least 3. This can be accomplished by dividing the plurality of consecutive beats into a plurality of sets of N consecutive beats, and for each set of N consecutive beats, selecting 2 of the N beats to produce a sub-set of 2 beats per set of N consecutive beats. For example, in a specific embodiment, the first 2 beats from each set of N beats are selected.

Time domain data, associated with the plurality of sub-sets of 2 beats, is transformed to frequency domain data. Then, there is a determination, based on the frequency domain data, of the patient's myocardial mechanical stability. In specific embodiments the alternans magnitude at 0.5 cycles/beat is determined based on the frequency domain data, and myocardial mechanical stability is monitored based on the alternans magnitude at 0.5 cycles/beat. This can include, for example, determining, based on the alternans magnitude at 0.5 cycles/beat, whether mechanical alternans are present. In accordance with an embodiment, changes in the alternans magnitude at 0.5 cycles/beat is tracked over time to thereby track changes in myocardial mechanical stability.

In accordance with an embodiment, the patient's heart is paced for a period of time using a patterned pacing sequence that repeats every N beats, and the signal indicative of mechanical functioning of the patient's heart if obtained while the patient's heart is being paced using the patterned pacing sequence.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
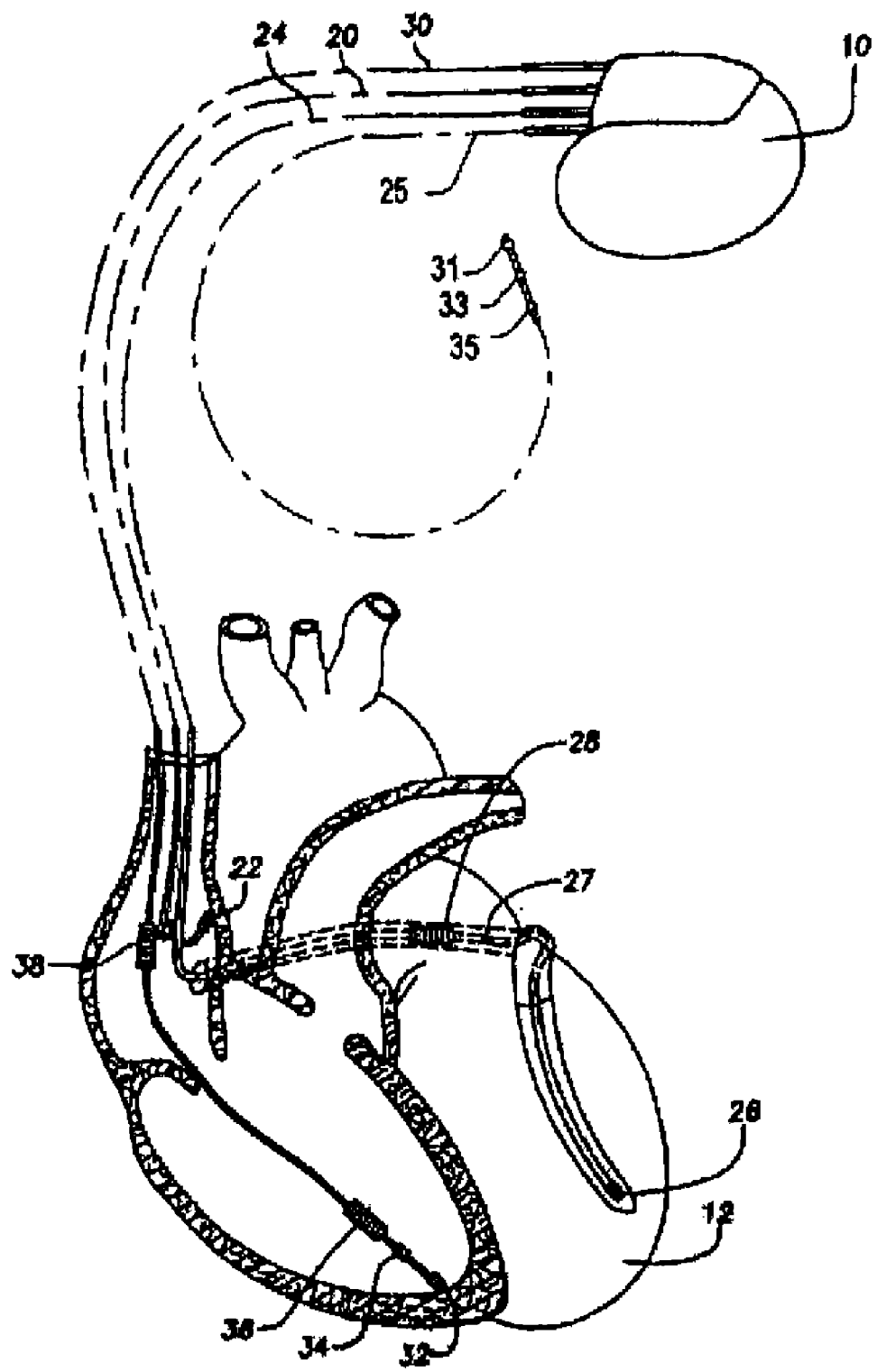
FIG. 1 is a simplified diagram illustrating an exemplary ICD in electrical communication with a patient's heart.
Figure 2:
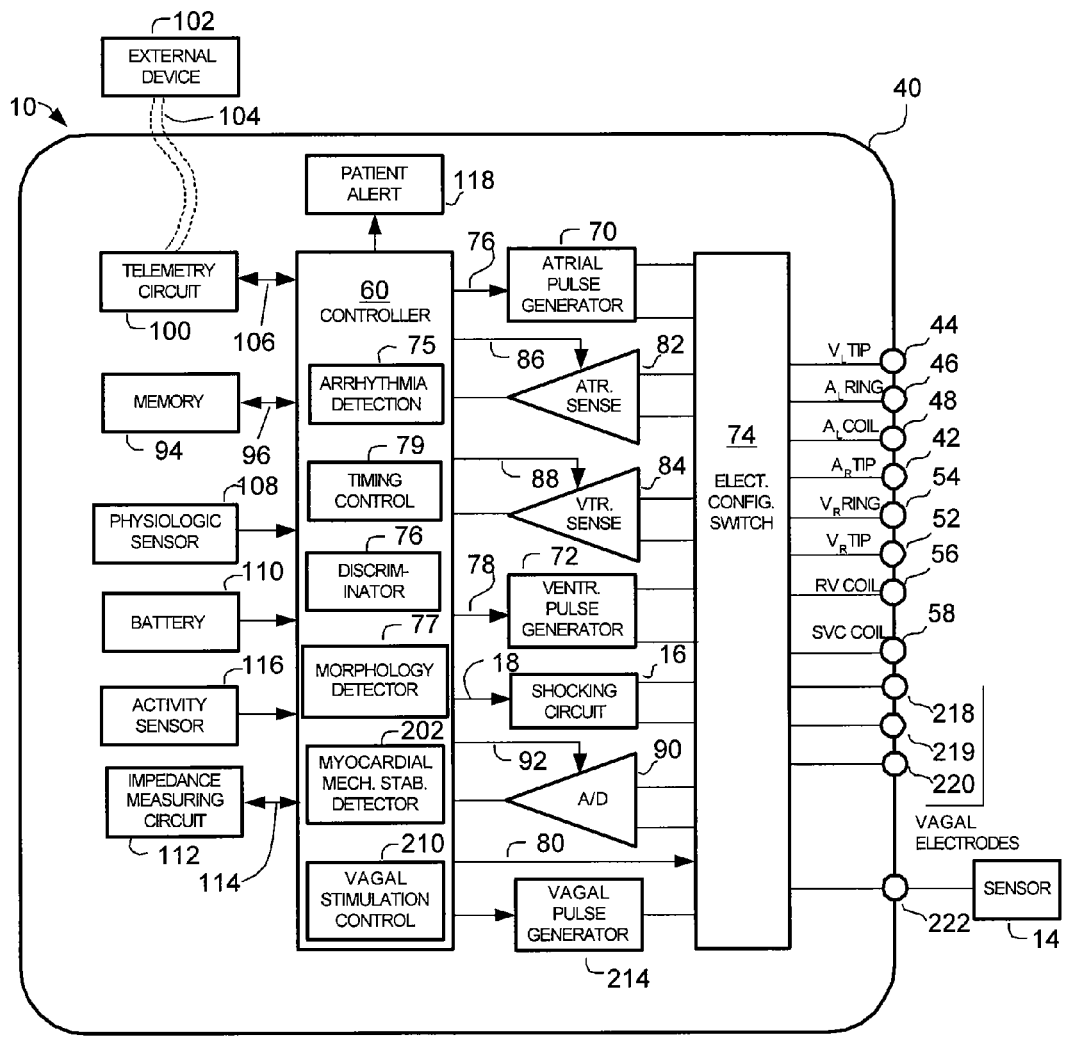
FIG. 2 is a functional block diagram of an exemplary ICD that can provide cardioversion, defibrillation, and pacing stimulation in four chambers of a heart, and detect the presence of mechanical alternans, in accordance with embodiments of the present invention.

Before describing the invention in detail, it is helpful to describe an example environment in which the invention may be implemented. The present invention is particularly useful in the environment of an implantable cardiac device that can monitor mechanical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

One of the above described leads (or a further lead) can also connect a further sensor (not specifically shown in FIG. 1, but shown as sensor 14 in FIG. 2) to the ICD 10, where the further sensor 14 is capable of measuring the mechanical functioning of the heart, or a surrogate thereof. In one embodiment, the sensor 14 is a pressure transducer that obtains measures of ventricular pressure. In another embodiment, the sensor 14 is an accelerometer that obtains measures of contraction strength. In a further embodiment, the sensor 14 is a blood flow transducer that obtains measures of blood flow rate. In still another embodiment, the sensor 14 is an acoustic transducer that obtains measures of heart sounds. Such an acoustic transducer can be, e.g., a microphone or an accelerometer that responds to acoustic vibrations transmitted through body fluids, to thereby detect alternating loud and soft sounds. In a further embodiment, the sensor 14 is an impedance measuring circuit having voltage sense electrodes to measure volumetric alternans, which is a surrogate of mechanical alternans. In still another embodiment, the sensor 14 is a photoplethysmography (PPG) sensor that measure pulse pressure. In a further embodiment, the sensor is a venous oxygen saturation (SVO2) sensor that measures venous oxygen saturation levels, which are believed to be indicative of mechanical functioning of the heart. These are just some examples of sensors that are capable of measuring the mechanical functioning of the heart, or a surrogate thereof. Other types of sensors capable of measuring the mechanical functioning of the heart, or a surrogate thereof, are also within the scope of the present invention.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking, the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts. Additionally, where the sensor 14 is connected to the ICD by its own lead, the connector can include a terminal 222, which is configured for connecting the sensor 14 to the ICD. It is also possible that the sensor 14 is integrated with the housing 40, and thus does not need to be connected via a terminal.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac perfor-mance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting mechanical alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes. The data acquisition system 90 (or a separate similar system) can also convert analog signals received from the sensor(s) 14 into digital signals that can be monitored by the myocardial mechanical stability detector 202 and/or stored in memory 94.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467

(Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

Also shown in FIG. 2 is the sensor 14 that is used to obtain a signal that is indicative of mechanical functioning of a patient's heart. As mentioned above, the sensor 14 can be: a pressure transducer that obtains measures of ventricular pressure; an accelerometer that obtains measures of contraction strength; a blood flow transducers that obtains measures of blood flow rate; an acoustic transducer that obtains measures of heart sounds; an impedance measuring circuit having voltage sense electrodes to measure volumetric alternans, which is a surrogate of mechanical alternans; a photo-plethysmography (PPG) sensor the measures pulse pressure; or a venous oxygen saturation (SVO2) sensor. Exemplary acoustic transducers are disclosed in U.S. Pat. No. 6,527,729 (Turcott), each of which is incorporated herein by reference. Exemplary implantable PPG sensors are disclosed in U.S. Pat. Nos. 6,409,675 (Turcott) and 6,731,967 (Turcott), and U.S. patent application Ser. Nos. 11/231,555 (Poore), filed Sep. 20, 2005, and 11/282,198 (Poore), filed Nov. 17, 2005, each of which is incorporated herein by reference. Exemplary pressure transducers are disclosed in U.S. patent application Ser. No. 11/072,942, filed Mar. 3, 2005 (Fayram et al.), which is incorporated herein by reference. These are just some examples of sensors that are capable of measuring the mechanical functioning of the heart, or a surrogate thereof. Other types of sensors capable of measuring the mechanical functioning of the heart, or a surrogate thereof, are also within the scope of the present invention.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

Mechanical Alternans

Still referring to FIG. 2, in accordance with embodiments of the present invention, the microcontroller 60 includes a myocardial mechanical stability detector 202, which as described in more detail below, can monitor myocardial mechanical stability, e.g., by detecting the presence of mechanical alternans. The myocardial mechanical stability detector 202 can be implemented within the microcontroller 60, as shown in FIG. 2. Thus, myocardial mechanical stability detector 202 can be implemented by software, firmware, or combinations thereof. It is also possible that all, or portions, of the myocardial mechanical stability detector 202 can be implemented using hardware. Further, it is possible that all, or portions, of the myocardial mechanical stability detector 202 be implemented external to the microcontroller 60.

In an embodiment, the myocardial mechanical stability detector 202 triggers data acquisition circuit 90 and timing control circuit 79 to acquire a signal that is indicative of mechanical functioning of a patient's heart. Such a signal can be representative of an actual measure of mechanical functioning, or representative of a surrogate of mechanical functions. For an example, such a signal, if obtained from a pressure transducer within a ventricle, can be representative of ventricular pressure. In another embodiment, the signal is representative of contraction strength, which can be obtained from an accelerometer. In a further embodiment, the signal is representative of blood flow rate, which can be obtained from a blood flow transducer. In another embodiment, the signal is representative of heart rate sounds, which can be obtained from a microphone or an accelerometer that responds to acoustic vibrations transmitted through body fluids. In still another embodiment, the signal can representative of blood volume, which can be obtained using an impedance measuring circuit. In still another embodiment, the signal can be representative of pulse pressure, which can be obtained using a photo-plethysmography sensor. In still another embodiment, the signal can be representative of venous oxygen saturation (SVO2). Each of the above elements are exemplary sensors that can be used to acquire a signal that is representative of mechanical functioning of a patient's heart, or a surrogate thereof. One of ordinary skill in the art, based on the disclosure herein, would understand that other types of sensors are also within the scope of the present invention.

Each of the above described signals are cyclical because they are indicative of the mechanical functioning of the heart, with each cycle of the signal corresponding to a beat of the patient's heart. The myocardial mechanical stability detector 202 can measure metrics of each cycle of the signal (i.e., metrics of each beat), to thereby determine whether there is an alternation in such metrics. Examples of such metrics include, but are not limited to, amplitude, width, area, and morphology. Depending on the signal being analyzed, the metrics can also be of specific portions or markers within the signal. The myocardial mechanical stability detector 202 can also trigger the implantable device 10 to respond appropriately when mechanical alternans are detected, as will be explained in more detail below. Additionally, in conjunction with the telemetry circuit 100, the myocardial mechanical stability detector 202 can be configured to deliver status information, relating to the patient's myocardial mechanical stability, to the external device 102 through an established communication link 104. The myocardial mechanical stability detector 202 may also trigger a patient or physician alert in response to detecting mechanical alternans. For example, a patient alert 118, which produces a vibratory or auditory alert, may be triggered by the myocardial mechanical stability detector 202.

Electrical alternans, such as Twave alternans have been demonstrated in many studies to be strong predictor of mortality, independent of left ventricular ejection fraction (LVEF). It had been generally believed that an elevated constant heart rate is a requirement for the detection of Twave alternans. However, a recent work published by Bulling a et al., entitled "Resonant Pacing Improves Twave Alternans Testing in Patients with Dilated Cardiomyopathy" (Heart Rhythm v1:S129, 2004) revealed a more robust detection with "resonant pacing" scheme. In this technique, Twave alternans with higher amplitudes were detected by pacing at a relatively shorter interval periodically once every fourth cycle during a moderately fast and constant pacing routine. This is an example of a patterned pacing sequence that repeats every 4 beats. Other examples of patterned pacing sequences are disclosed in U.S. patent application Ser. No. 10/884,276 (Bulling a), filed Jan. 6, 2005, (Publication No. US 2005/0004608), entitled "System and Method for Assessment of Cardiac Electrophysiologic Stability and Modulation of Cardiac Oscillations," which is incorporated herein by reference. Further examples of patterned pacing sequences are disclosed in U.S. patent application Ser. No. 11/341,086 (Farazi), filed Jan. 27, 2006, entitled "Pacing Schemes For Revealing Twave Alternans (TWA) at Low to Moderate Heart Rates," which is also incorporated herein by reference. The inventors of the present invention believe that such patterned pacing will also reveal mechanical alternans at lower heart rates. Thus, in certain embodiments of the present invention, as will be described below, a patient is paced using a patterned pacing sequence that repeats every N beats, where N is an integer. Some embodiments of the present invention can also be used where the patient is paced using a constant elevated heart rate and/or when the patient is not paced at all.

By pacing a patient's heart with a patterned pacing sequence, the expected alternans pattern is known. For example, if the patterned pacing sequence repeats every 3 beats, then it is expected that there will be an ABCABC ABC . . . alternans pattern; if the patterned pacing sequence repeats every 4 beats, then it is expected that there will be an ABCDABCDABCD . . . alternans pattern; and so on. In accordance with specific embodiments of the present invention, because patterned pacing sequences are being used to induce specific expected mechanical alternans patterns, analysis of the alternans can be optimized to match the pattern being induced.

Figure 3:
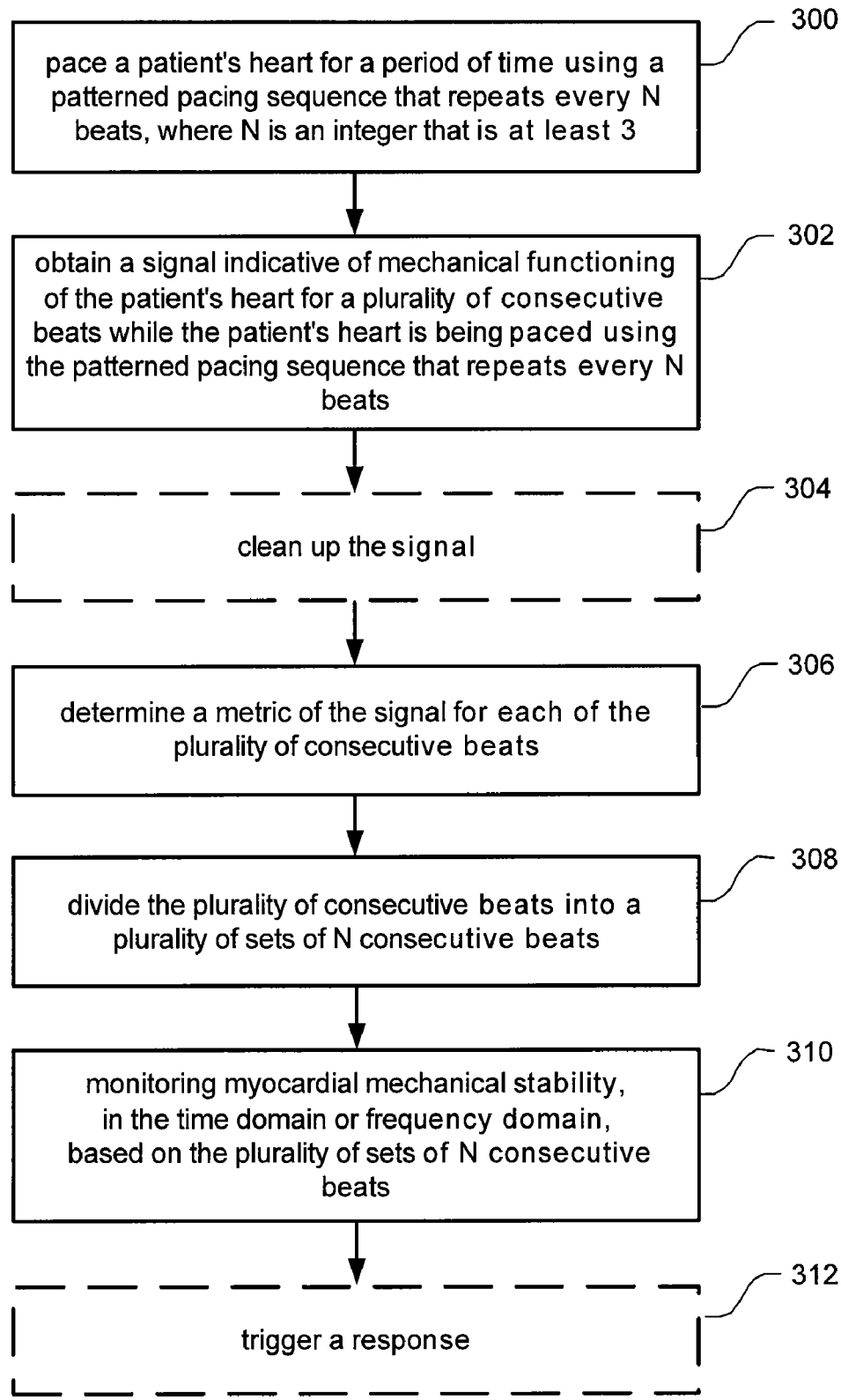
FIG. 3 is a high-level flow diagram that is useful for describing embodiments of the present invention that are used to monitor myocardial mechanical stability.

Specific embodiments of the present invention will now be summarized with reference to the high level flow diagram of FIG. 3. In this flow diagram, and the other flow diagrams described herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of the cardiac device. Those skilled in the art may readily write such a control program based on the flow diagrams and other descriptions presented herein. The steps of the flow diagram can be implemented, e.g., by an implantable cardiac device, such as but not limited to ICD 10. It is also possible that certain steps can be implemented by a non-implantable device.

At step 300, a patient's heart is paced for a period of time using a patterned pacing sequence that repeats every N beats, where N is an integer that is at least 2. In specific embodiments, N is at least 3. The term patterned pacing sequence as used herein refers to a repeatable pacing sequence where at least one paced beat's cycle length differs from another paced beat's cycle length. For example, assuming N=4, the patterned pacing sequence used to pace the patient's heart can include 3 consecutive beats having a baseline cycle length (CL) followed by a shortened beat (i.e., CL−Δt). In another example, also assuming N=4, the patterned pacing sequence can include 3 consecutive beats having a baseline cycle length (CL) followed by a lengthened beat (i.e., CL+Δt). In another example where N=4, the patterned pacing sequence can include successively shortened beats (e.g., CL, CL−Δt, CL−2Δt and CL−3Δt). These are just a few examples of patterned pacing sequences, which are not meant to be limiting. Other example are provided in the patent applications which were incorporated by reference above. To ensure capture, each beat of the patterned pacing sequence should be shorter than an intrinsic beat. Additionally, where the patient is normally paced, each paced beat of a patterned pacing sequence should be shorter than a beat length corresponding to the patient's normal pacing. In accordance with an embodiment, the pacing performed at step 300 is performed by an implantable cardiac device (e.g., ICD 10).

At step 302, a signal is obtain that is indicative of mechanical functioning of the patient's heart for a plurality of consecutive beats while the patient's heart is being paced using the patterned pacing sequence that repeats every N beats. Such a signal can be representative of an actual measure of mechanical functioning, or representative of a surrogate of mechanical functions. In accordance with an embodiment, the signal is representative of ventricular pressure, and is obtained from a pressure transducer within a ventricle. In another embodiment, the signal is representative of contraction strength and is obtained from an accelerometer. In a further embodiment, the signal is representative of blood flow rate and is obtained from a blood flow transducer. In another embodiment, the signal is representative of heart rate sounds and is obtained from a microphone or an accelerometer that responds to acoustic vibrations transmitted through body fluids. In still another embodiment, the signal is representative of blood volume and is obtained using an impedance measuring circuit. In still another embodiment, the signal is representative of pulse pressure and is obtained using a photoplethysmography sensor. In another embodiment, the signal is representative of venous oxygen saturation and is obtained using an SVO2 sensor. Each of the above elements are exemplary sensors that can be used to acquire a signal that is indicative of mechanical functioning of a patient's heart. One of ordinary skill in the art, based on the disclosure herein, would understand that other types signals obtained from other types of sensors are also within the scope of the present invention. In accordance with an embodiment, data indicative of the signal is stored within the ICD 10 (e.g., in memory 94).

At an optional step 304, the signal obtained at step 302 is cleaned up. This can be accomplished, e.g., by filtering the signal (or data indicative of the signal) and/or removing noisy cycle segments of the signal. Filtering the signal could include, e.g., the use of a low-pass filter with a cutoff frequency of about 250 Hz. Additionally, a high-pass filter can be used to reduce the contribution of DC-offsets and respiration drift to the signal. Removal of noisy cycles can be accomplished, e.g., by removing any number of cycles that are exposed to severe noise, e.g., from myopotentials or electromagnetic interference. A further optional step is to resample stored cycles of the signal to match in length. For example, if a signal were originally sampled at 256 Hz, it could be upsampled to 1000 Hz, stretched or compressed to match a mean cycle length, and then down-sampled again to 256 Hz. The above described pre-processing to clean up the signal generally helps to minimize noise in the signal. Step 304 can also include removing easily detected ectopic beats (e.g., premature contractions of the ventricles). For example, this can be accomplished by comparing each cardiac length to a mean cardiac length. An ectopic beat can then be identified where a length of a beat is less than a threshold percentage (e.g., 80%) of the mean length, yet is surrounded by beats having lengths that are greater than the threshold percentage.

At step 306, a metric of the signal is determined for each of the plurality of consecutive beats. As explained above, the metric can be include maximum amplitude, peak-to-peak amplitude, width, area, morphology, or the like. At step 308, the plurality of consecutive beats (of the signal obtained at step 302, and optionally cleaned up at step 304) are divided into a plurality of sets of N consecutive beats. For an example, which is not meant to be limiting, assume the obtained signal is representative of 1000 beats, and N=4 (as in the examples discussed above), then step 308 would include dividing the 1000 beats into 250 sets of 4 consecutive beats. The order of certain steps is not important, unless a certain step is using the results of an earlier step. For example, step 306 can be performed before, after, or at the same time as step 308.

At a next step 310, a patients' myocardial mechanical stability is monitored based on the plurality of sets of N consecutive beats. Such monitoring can be performed in the time domain, as discussed with reference to the FIG. 4, or in the frequency domain, as discussed with reference to FIG. 9.

At an optional step 312, an appropriate response can be trigger. For example, if it is determined at step 310 that an alternans magnitude is beyond a threshold, then an appropriate response can be triggered. For completeness, exemplary responses are discussed below.

Time Domain Analysis

One way to monitor a patient's myocardial mechanical stability (e.g., to determine if mechanical alternans are present), in the time domain, based on the plurality of sets of N consecutive beats, is to simply average metrics of corresponding beats from each set. A determination of myocardial mechanical stability (e.g., whether mechanical alternans are present) can then be made based on the averaged metrics. For example, assume that the desire is to determine whether mechanical alternans are present based on 250 sets of 4 consecutive beats (i.e., each set includes a beat pattern ABCD). Also assume that the metric being measured for each cycle of the signal (which corresponds to a beat) is maximum amplitude. The maximum amplitudes of each of the 250 "A" cycles/beats can be averaged, the maximum amplitudes of each of the 250 "B" cycles/beats can be averages, the maximum amplitudes of each of the 250 "C" cycles/beats can be averaged, and the maximum amplitudes of each of the 250 "D" cycles/beats can be averaged, resulting in average maximum amplitudes for cycles/beats ABCD. A difference between the average "A" maximum amplitude and the average "B" maximum amplitude can then be determined, as can the difference between the average "B" maximum amplitude and the average "C" maximum amplitude, and the difference between the average "C" maximum amplitude and the average "D" maximum amplitude. A determination of whether mechanical alternans are present can then be based on whether such differences exceed corresponding thresholds. A potential problem with performing the averaging suggested above is that such averaging may mask or bury important information included within the sets of N consecutive beats. For example, if there is a phase reversal, an ectopic beat, or another type of disruptive beat within one of the sets, the averaging as suggested above may mask such information. Additionally, large noise artifacts may corrupt the results of such averaging.

Figure 4:
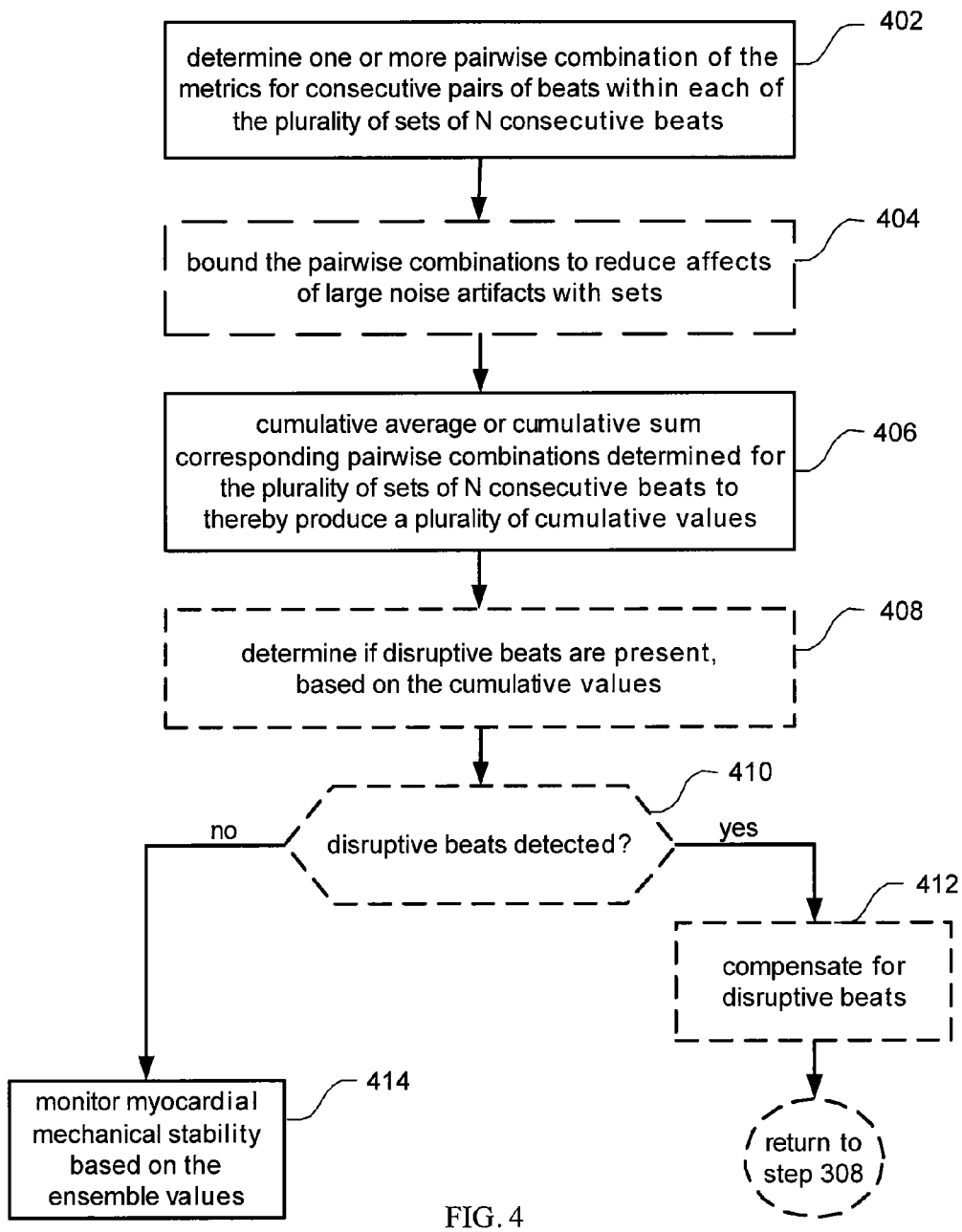
FIG. 4 is a high-level flow diagram that is useful for describing time domain embodiments of the present invention.

FIG. 4 is a high level flow diagram useful for describing embodiments of the present invention that relate to monitoring myocardial mechanical stability at step 310, in the time domain, based on the plurality of sets of N consecutive beats produced at step 308.

Referring to FIG. 4, at step 402 one or more pairwise combination of the metrics for consecutive pairs of beats are determined for each of the plurality of sets of N consecutive beats. For example, assuming that N=4, and thus, that each set of N consecutive beats includes beats A, B, C and D (i.e., beat pattern ABCD), then pairwise combinations can be produced for beat pair AB, beat pair BC and/or beat pair CD. For simplicity, it will be assumed that pairwise combinations are produced only for beat pair AB, for each set of 4 consecutive beats.

In accordance with an embodiment of the present invention, each pairwise combination determined at step 402 is a pairwise difference. In other words, the pairwise combination for beat pair AB (referred to as $S_{AB}$) is equal to a metric of beat A minus a corresponding metric of beat B (i.e., $S_{AB}$=metric A−metric B). For simplicity, it will be assumed that the metric being used is maximum amplitude of a beat cycle. Thus, an exemplary pairwise combination for beat pair AB is equal to the amplitude of beat A minus the amplitude of beat B (i.e., $S_{AB}$=amplitude (A)−amplitude (B)). Continuing with the example that 1000 beats are separated into 250 sets of 4 consecutive beats, this will result in 250 $S_{AB}$ values (e.g., $S_{AB1}$=amplitude $(A_1)$−amplitude $(B_1)$; $S_{AB2}$=amplitude $(A_2)$−amplitude $(B_2)$; $S_{AB3}$=amplitude $(A_3)$−amplitude $(B_3)$, etc.). If pairwise combinations are also produced for beat pair BC and/or beat pair CD, then there would also be 250 $S_{BC}$ values (e.g., $S_{BC1}$=amplitude $(B_1)$−amplitude $(C_1)$; $S_{BC2}$=amplitude $(B_2)$−amplitude $(C_2)$; $S_{BC3}$=amplitude $(B_3)$−amplitude $(C_3)$, etc.) and/or 250 $S_{CD}$ values (e.g., $S_{CD1}$=amplitude $(C_1)$−amplitude $(D_1)$; $S_{CD2}$=amplitude $(C_2)$−amplitude $(D_2)$; $S_{CD3}$=amplitude $(C_3)$−amplitude $(D_3)$, etc.).

In accordance with another embodiment of the present invention, each pairwise combination determined at step 402 is a pairwise summation. In other words, the pairwise combination for beat pair AB (referred to as $S_{AB}$) is equal to a metric of beat A plus a corresponding metric of beat B (i.e., $S_{AB}$=metric A+metric B). In still another embodiment of the present invention, each pairwise combination determined at step 402 is a pairwise average. In other words, the pairwise combination for beat pair AB (referred to as $S_{AB}$) is equal to an average of a metric of beat A and a metric of beat B (i.e., $S_{AB}$=avg(metric A+metric B)). These are just a few examples of pairwise combinations. Other types of pairwise combinations are also within the scope of the present invention.

Figure 5:
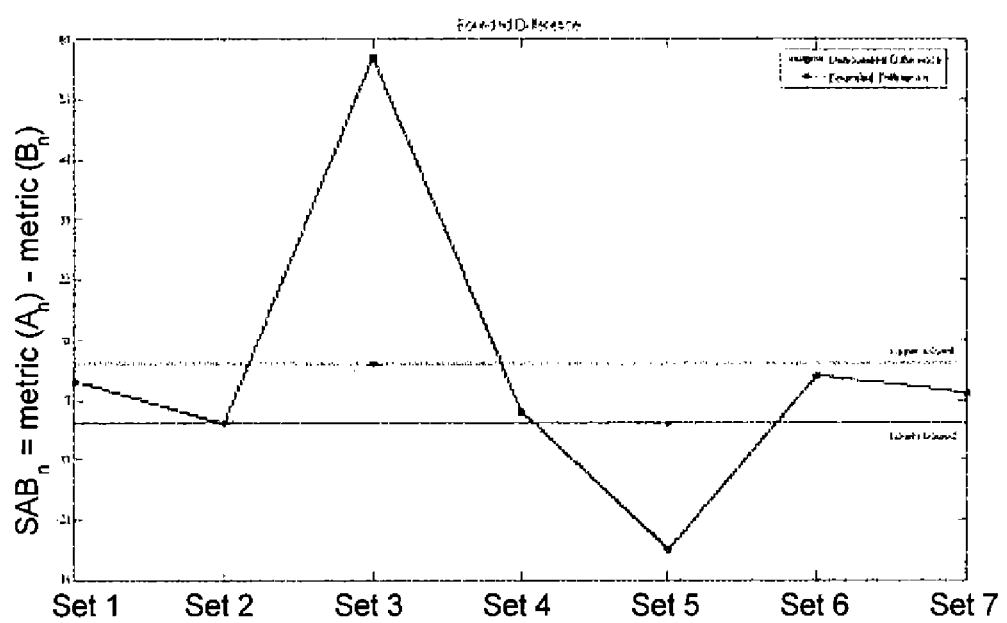
FIG. 5 is a graph that is useful for describing how pairwise combinations can be bound, in accordance with embodiments of the present invention.

A next step 404, which is optional, but preferred, is to bound the pairwise combinations produced at step 402, to minimize the effect of large noise artifacts. An example of this is shown in FIG. 5, where pairwise differences are limited by an upper bound=6, and a lower bound=4. The precise bound values can be determined, e.g., through experimentation. The bound values can be specific to a patient, or specific to a population.

Returning to FIG. 4, at step 406, corresponding pairwise combinations (determined for the plurality of sets of N consecutive beats) are cumulative averaged or cumulative summed to thereby produce a plurality of cumulative values (G). For example, where the pairwise combinations are cumulative averaged, then the cumulative values $G_n$=avg($S_1$+ $S_2$ . . . +$S_n$). For a more specific example, $G_{AB1}$=$S_{AB1}$; $G_{AB2}$=avg($S_{AB1}$+$S_{AB2}$); $G_{AB3}$=avg($S_{AB1}$+$S_{AB2}$+$S_{AB3}$); . . . and $G_{ABn}$=avg($S_{AB1}$+$S_{AB2}$+$S_{AB3}$ . . . +$S_{ABn}$). Where the pairwise combinations are cumulative sums, then the cumulative values $G_n$=sum ($S_1$+$S_2$ . . . +$S_n$) e.g., $G_{AB1}$=$S_{AB1}$; $G_{AB2}$=sum ($S_{AB1}$+$S_{AB2}$); $G_{AB3}$=sum ($S_{AB1}$+$S_{AB2}$+$S_{AB3}$); . . . and $G_{ABn}$=sum ($S_{AB1}$+$S_{AB2}$+$S_{AB3}$ . . . +$S_{ABn}$).

At a next step 408, which along with steps 410 and 412 are optional, but preferred, one or more disruptive beat(s) are detected, if present, based on the cumulative values. Steps 408-412 are especially useful if optional step 306 was not performed, or if step 306 did not include removing easily detected ectopic beats (e.g., identified where a cycle length of a beat is less than a threshold percentage e.g., 80% of the mean cycle length, yet is surrounded by beats having cycle lengths that are greater than the threshold percentage). Even if easily detected ectopic beats were removed at step 306, steps 408-412 are useful to remove more difficult to detect ectopic beats, or other types of disruptive beats.

Disruptive beats, which can include ectopic beats, are caused by an irregularity of heart rate and/or heart rhythm involving extra or skipped beats. More generally, a disruptive beat, as the term is used herein, is any beat in a series of beats that offsets a regular beat pattern by a non-multiple of N, where N is the number of beats after which the beat pattern repeats. For instance if N=4, and a sequence begins as $A_1B_1C_1D_1A_2B_2C_2D_2$ $A_3B_3C_3D_3A_4B_4A_5B_5C_5D_5$ then the bolded $A_4B_4$ describes two disruptive beats. Many ectopic type disruptive beats may have already been removed at step 306, which was discussed above. However, there may be some ectopic beats not identified in the simple algorithm (i.e., the simple threshold comparison) used in step 306. Further, there are other types of disruptive beats that would not be identified using the simple algorithm of step 306. Further, since step 306 is optional, it is possible that no ectopic beats are removed at step 306.

If disruptive beats are detected, then they are compensated for at step 412, e.g., by removing or replacing the disruptive beats, or by inserting extra beats. The method then returns to step 308, so that pairwise combinations can be recalculated at step 402, with the disruptive beats removed, replaced, or extra beats inserted. If disruptive beats $A_4B_4$ are removed, then beats $A_5B_5C_5D_5$ become beats $A_4B_4C_4D_4$. If disruptive beats are $A_4B_4$ are replaced, they can be replaced, e.g., with an average beat set $A_{avg}B_{avg}C_{avg}D_{avg}$, or a beat set equal to the previous beat set (e.g., $A_3B_3C_3D_3$). If extra beats are inserted, then extra beats $C_4D_4$ can be inserted after $A_4B_4$, e.g., where values for beats $C_4D_4$ can be an average of previous C and D values (i.e., $C_4$=avg($C_1$+$C_2$+$C_3$; and $D_4$=avg($D_1$+$D_2$+$D_3$), or equal to the C and D values from the previous beat set (i.e., $C_4$=$C_3$; and $D_4$=$D_3$). These are just a few examples of how disruptive beats can be compensated for at step 412, which are not meant to be limiting. One of ordinary skill in the art would appreciate from this description that alternatives ways of compensating for disruptive beats are possible, which are also within the scope of the present invention. Details of unique ways of detecting disruptive beats based on cumulative values, in accordance with embodiments of the present invention, are discussed below with reference to FIGS. 8A and 8B.

At step 414 myocardial mechanical stability is monitored based on the cumulative values. As explained above, this step preferably occurs after disruptive beats, if present, are compensated for at steps 408-412. If optional steps 408-412 are not performed, then flow would go directly from step 406 to step 414. In specific embodiments, step 414 includes determining, based on the cumulative values, whether mechanical alternans are present. In other embodiments, step 414 includes tracking changes in myocardial mechanical stability over time. Step 414 will now be described in more detail with reference to FIGS. 6A and 6B and FIGS. 7A and 7B.

Figure 6A:
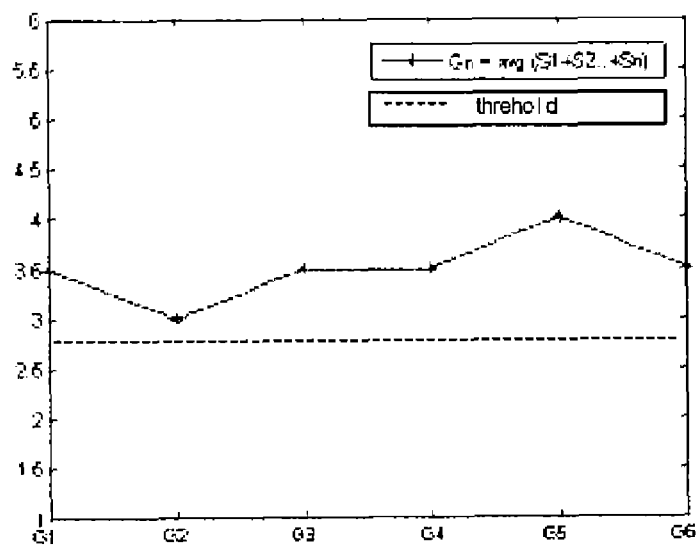
FIGS. 6A and 6B are graphs that are useful for describing how of cumulative average values can be used to detect the presence of mechanical alternans, in accordance with embodiments of the present invention.
Figure 6B:
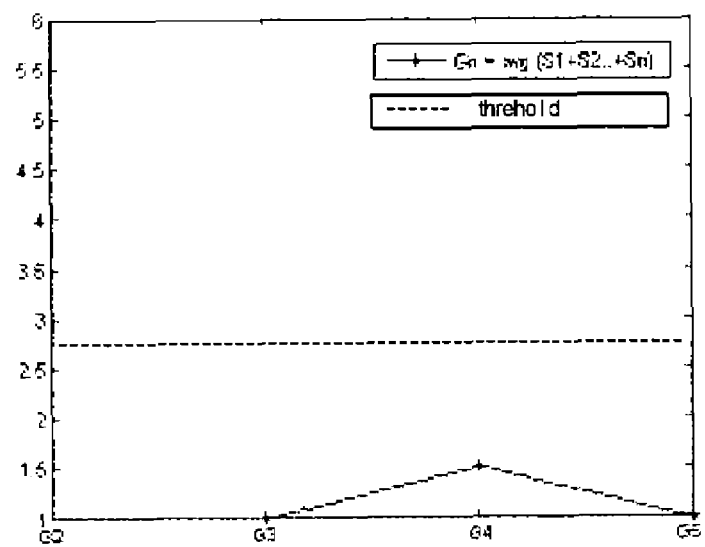

FIG. 6A is an exemplary graph of cumulative average values when mechanical alternans are present, and FIG. 6B is an exemplary graph of cumulative average values when mechanical alternans are not present. As can be appreciated from FIGS. 6A and 6B, when mechanical alternans are present the cumulative average values remain above a threshold (represented by a dashed line), and when mechanical alternans are not present the cumulative average values remain below the threshold. Accordingly, in embodiments where cumulative values (G) are cumulative average values, the presence of mechanical alternans can be determined by comparing cumulative average values to a threshold. Such a threshold can be determined, e.g., through experimentation. The threshold can be specific to a patient, or specific to a population.

In another embodiment, changes in myocardial mechanical stability can be monitored by tracking changes in cumulative average values that are obtained from time to time (e.g., once a day, week, month or other time period). For example, if the cumulative average values increase over time, then it can be determined that the patient's myocardial mechanical stability is worsening. If the cumulative average values decrease over time, then it can be determine that the patient's myocardial mechanical stability is improving.

Figure 7A:
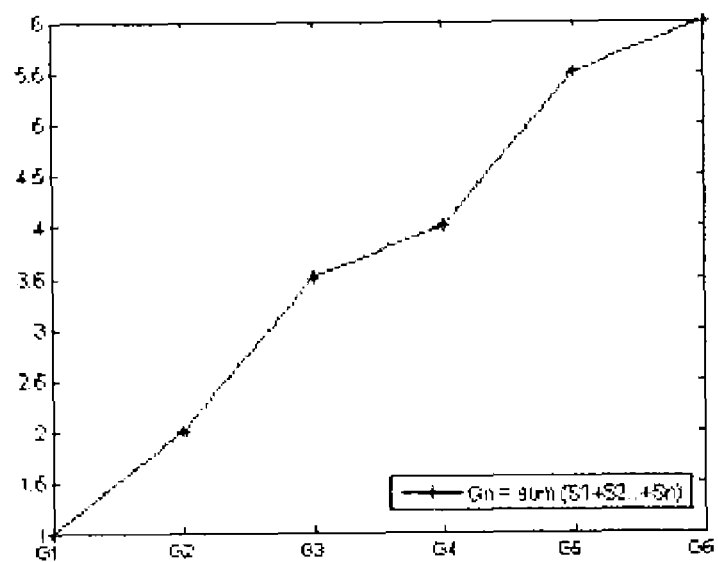
FIGS. 7A and 7B are graphs that are useful for describing how of cumulative sum values can be used to detect the presence of mechanical alternans, in accordance with embodiments of the present invention.
Figure 7B:
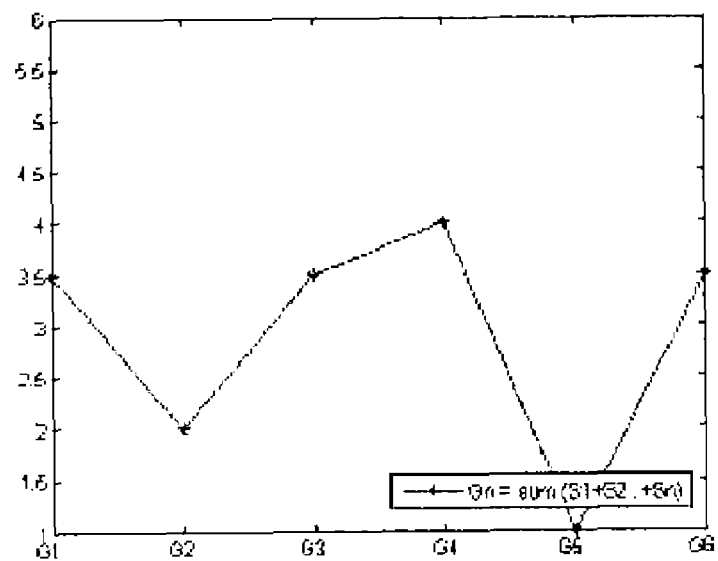

FIG. 7A is an exemplary graph of cumulative sum values when mechanical alternans are present, and FIG. 7B is an exemplary graph of cumulative sum values when mechanical alternans are not present. As can be appreciated from FIGS. 7A and 7B, where mechanical alternans are present the cumulative sum values continually increase, and where mechanical alternans are not present the cumulative sum values do not continually increase (but rather, go up and down in a generally random manner). Accordingly, in embodiments where cumulative values (G) are cumulative sum values, the presence of mechanical alternans can be determined, e.g., by comparing a slope of the cumulative sum values to a slope threshold. Alternatively, it can be determined that mechanical alternans are present when at least a specific number of consecutive cumulative sum values increase in value.

In another embodiment, changes in myocardial mechanical stability can be monitored by tracking changes in the cumulative sum values that are obtained from time to time (e.g., once a day, week, month or other time period). For example, if the slope of the cumulative sum values increases over time, then it can be determined that the patient's myocardial mechanical stability is worsening. If the slope of the cumulative sum values decreases over time, then it can be determine that the patient's myocardial mechanical stability is improving.

Specific embodiments of the present invention are also directed to the monitoring myocardial mechanical stability based on cumulative values, where a patient's heart is not paced, as well as where N is the integer 2.

Detecting Disruptive Beats in the Time Domain

As mentioned above, by using cumulative values, such as cumulative averages or cumulative sums, embodiments of the present invention provide unique ways in which disruptive beats can be detected. This will now be described with reference to FIGS. 8A and 8B.

Figure 8A:
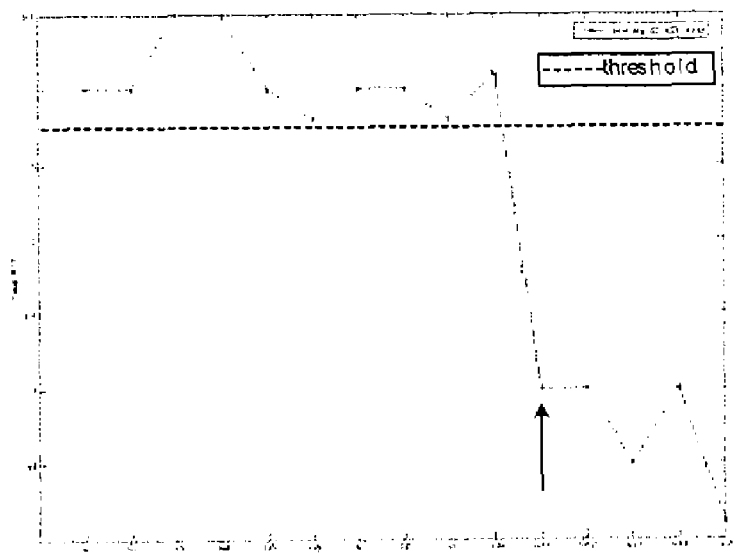
FIG. 8A is a graph that is useful for describing how cumulative average values can be used to detect disruptive beats, in accordance with embodiments of the present invention.

FIG. 8A is an exemplary graph of cumulative average values when mechanical alternans are present, but a disruptive beat is also present. In this example, a disruptive (e.g., missing or extra) beat can be detected when the cumulative average values stay consistently within one range of values and then suddenly shift into another (e.g., lower) range of values, e.g., within a few beats or specified short amount of time. For example, if at least X consecutive cumulative average values are within a predefined range, followed by at least X further consecutive cumulative average values within a different predefined range, then it can be determined that a disruptive beat caused the sudden change in the range of cumulative average values. It is the use of cumulative averaging of pairwise combinations that enables disruptive beats to be detected in this manner. The arrow in FIG. 8A shows that the disruptive beat occurs in $11^{th}$ set of N beats which was used to determine pairwise combination $S_{11}$.

Figure 8B:
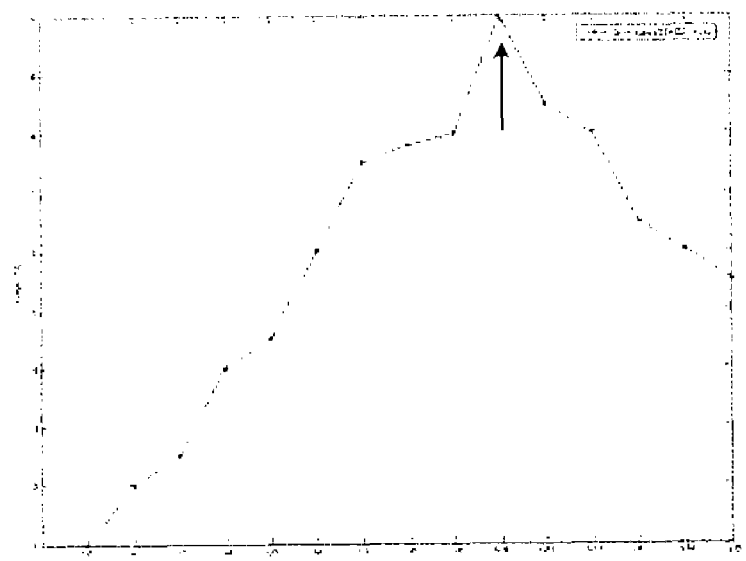
FIG. 8B is a graph that is useful for describing how cumulative sum values can be used to detect disruptive beats, in accordance with embodiments of the present invention.

FIG. 8B is an exemplary graph of cumulative sum values when mechanical alternans are present, but a disruptive beat is also present. In this example, a disruptive beat can be detected when the cumulative sum values consistently increase for a predetermined number of beats or amount of time, and then suddenly consistently decrease for a predetermined number of beats or amount of time. For example, if there are at least X consecutive cumulative sum values that increase in value, followed by at least X further consecutive cumulative sum values that decrease in value, then it can be determined that a disruptive beat caused the sudden change in cumulative average values. For another example, if the cumulative values have a consistently positive slope followed by a consistently negative slope, then it can be determined that a disruptive beat caused the sudden change in slope of cumulative values. It is the use of cumulative summing of pairwise combinations that enable disruptive beats to be detected in this manner. The arrow in FIG. 8B shows that the disruptive beat occurs in $11^{th}$ set of N beats which was used to determine pairwise combination $S_{11}$.

As was mentioned above in the discussion of step 408 (of FIG. 4), when disruptive beats are detected they should be compensated for, e.g., by removing the disruptive beats, replacing the disruptive beats, or inserting additional beats. After they are compensated for, the algorithm returns to step 308 (of FIG. 3) so that after the disruptive beats are removed, replaced, or additional beats are inserted, the revised beats (with the disruptive beats removed or replaced, or with beats added) can be re-divided up into a plurality of sets of N beats. Then, step 310 is repeated, which, as described above, can include repeating steps 402 through 410 with the revised plurality of sets of N consecutive beats.

Where N=4, for example, and it is determined using one of the above embodiments that a disruptive beat occurs within certain set of N beats, there need not be a determination of which beat within the N beat set is the disruptive beat. Rather, a single beat can be removed (or added or replaced with 2 beats). This causes the shifting all of the following sets of N beats by one beat when the algorithm returns to step 308, after the disruptive beats are removed or replaced. At that point the beats (with a disruptive beat, or a beat added) can be re-divided up into a plurality of sets of N beats, as mentioned above. If it still appears that a disruptive beat exists (at step 410), then once again a single beat can be removed (or added or replaced with 2 beats) thereby shifting all of the following sets of N beats by another beat. One or two iterations will likely account for all the disruptive beats for the plurality of beats being analyzed at the time.

Frequency Domain Analysis

When frequency domain analysis is being used to determine whether there is an AB alternans pattern (i.e. an alternans pattern that repeats every 2 beats), time domain data is converted to the frequency domain, e.g., using a Fourier Transformation. Then a magnitude at 0.5 cycles/beat of the resulting frequency spectra is analyzed, e.g., by comparing the magnitude to a threshold. Further, if a patient's heart is paced using a patterned pacing sequence that repeats every 2 beats, which may result in an AB alternans pattern, then the frequency of interest is 0.5 cycles/beat. In other words, the frequency of interest to detect an alternans pattern that repeats every 2 beats is 0.5 cycles/beat.

As explained in the published Bulling a patent application, which was incorporated by reference above, if a patient's heart is paced using a patterned pacing sequence that repeats every 3 beats, which may result in an ABC electrical alternans pattern (i.e. an electrical alternans pattern that repeats every 3 beats), then the frequency of interest is 0.33 cycles/beat. Further, if a patient's heart is paced using a patterned pacing sequence that repeats every 4 beats, which may result in an ABCD electrical alternans pattern (i.e. an electrical alternans pattern that repeats every 4 beats), then the frequency of interest is 0.25 cycles/beat. In other words, Bulling a generally explains that when a patient's heart is paced using a patterned pacing sequence that repeats every N beats, then 1/N cycles/beat is the frequency of interest to determine whether electrical alternans are present.

When a patient is experiencing an AB alternans pattern (i.e. an alternans pattern that repeats every 2 beats), the measured frequency content at 0.5 cycles/beat is typically great enough to be distinguishable from noise. However, when a patient is experiencing an ABC alternans pattern (i.e. an alternans pattern that repeats every 3 beats), the measured frequency content at 0.33 cycles/beat may not be great enough to be distinguishable from noise. Further, when patient is experiencing an ABCD alternans pattern (i.e. an alternans pattern that repeats every 4 beats), the measured frequency content at 0.25 cycles/beat will even more likely not be great enough to be distinguishable from noise. Embodiments of the present invention, as described below with reference to FIGS. 9-12, overcome such problems.

Figure 9:
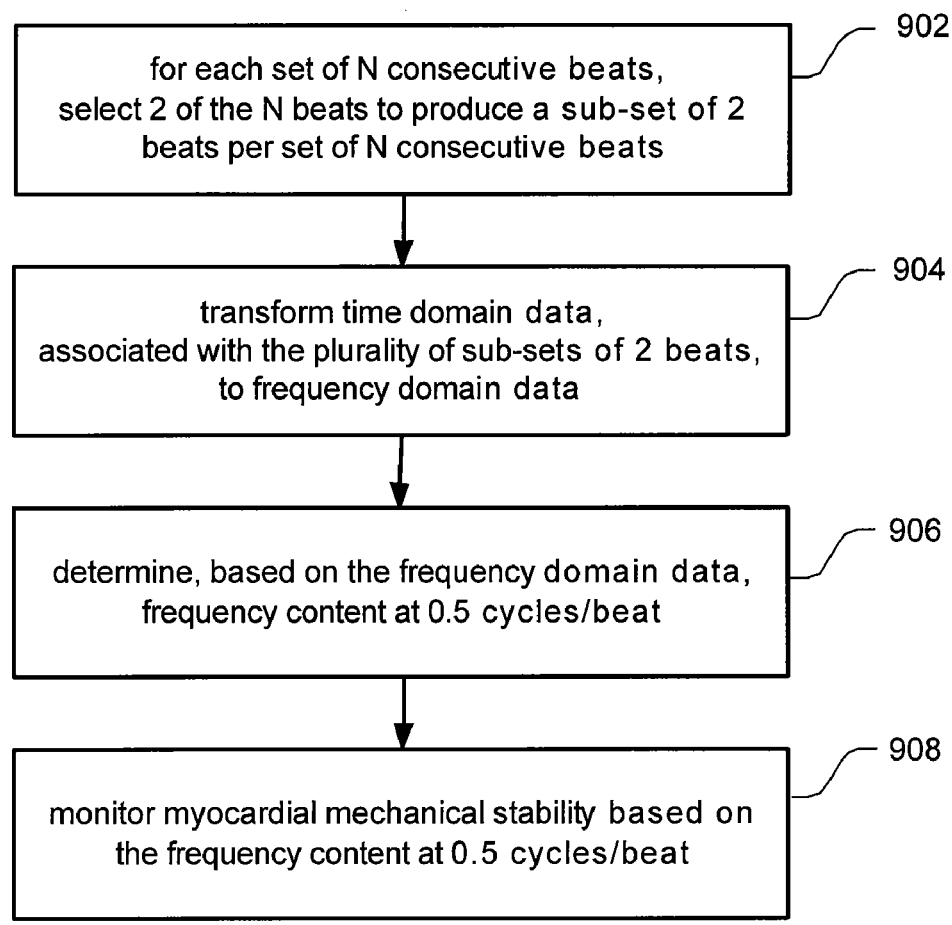
FIG. 9 is a high-level flow diagram that is useful for describing frequency domain embodiments of the present invention.

FIG. 9 is a high level flow diagram useful for describing embodiments of the present invention that relate to monitoring myocardial mechanical stability at step 310 (of FIG. 3), in the frequency domain, based on the plurality of sets of N consecutive beats produced at step 308 (of FIG. 3). When explaining the steps in FIG. 9, it will be assumed again for the sake of explanation that a patient is paced using a patterned pacing sequence that repeats every 4 beats (i.e., that N=4), and that 1000 beats are being analyzed. Thus, it is also assumed that the 1000 beats are separated into 250 sets of 4 consecutive beats at step 308.

Referring to FIG. 9, at step 902, for each set of N consecutive beats, 2 of the N beats are selected to produce a sub-set of 2 beats per set of N consecutive beats. Continuing with the example where N=4, at step 902, for each of the 250 sets of 4 consecutive beats, 2 of the 4 beats are selected to produce a sub-set of 2 beats per set of 4 consecutive beats. Were N=4, each set of N (i.e., 4) consecutive beats includes beats A, B, C and D (i.e., a beat pattern ABCD). Thus, at step 402, beats A and B, beats A and C, beats A and D, beats B and C, beats B and D, or beats C and D can be selected to produce the sub-sets of 2 beats per set of 4 consecutive beats. Preferably, the 2 beats selected at step 902 are consecutive beats (e.g., beats A and B, beats B and C, or beats C and D). A likely 2 beats to select are the first two 2 in the set (i.e., beats A and B), because it is believed that mechanical alternans are typically be most noticeable in the first 2 beats of each set. Accordingly, for the following discussion is it will be assumed that beats A and B (or simply beats AB) are selected at step 402, resulting in 250 sub-sets ($A_1B_1, A_2B_2 \ldots A_{250}B_{250}$). However, beats B and C (also simply referred to as beats BC) can be selected at step 402, resulting in 250 sub-sets ($B_1C_1, B_2C_2 \ldots B_{250}C_{250}$). Similarly, beats C and D could be selected.

Figure 10:
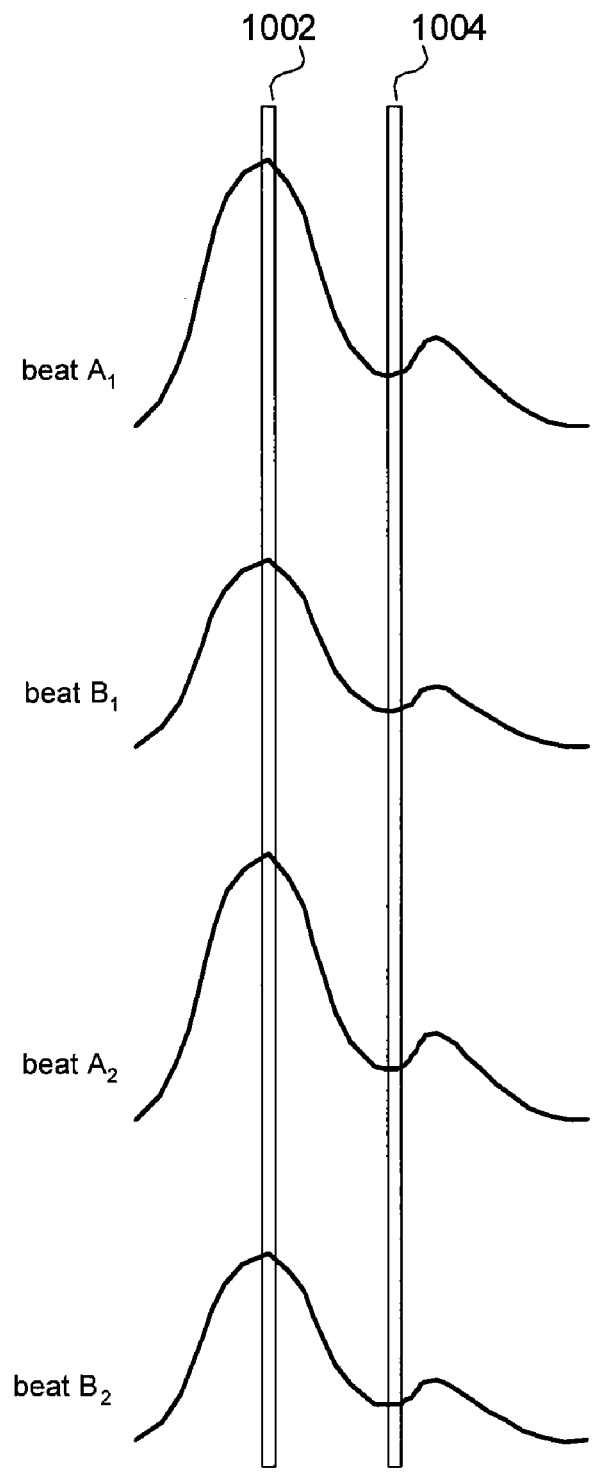
FIG. 10 is a graph that is useful for describing how a Fourier Transform or Fast Fourier Transform can be performed on time domain data.

Next, step 904 includes transforming time domain data, associated with the plurality of sub-sets of 2 beats produced at step 902, to frequency domain data. This can be accomplished, in accordance with a specific embodiment, by aligning the beats of the sub-sets (produced at step 902) to match in time. For example, assuming the signal indicative of mechanical functioning of the patient's heart for a plurality of consecutive beats is a photoplethysmography (PPG) signal, FIG. 10 illustrates aligning beats $A_1$ and $B_1$ of sub-set $A_1B_1$ with beats $A_2$ and $B_2$ of sub-set $A_2B_2$. For simplicity, the AB beats of sub-sets $A_3B_3$-$A_{250}B_{250}$ are not shown. The aligning of beats can be achieved, e.g., by matching the max amplitude for each beat, or by matching other beat markers, such as the dichroic notch of each beat in the PPG signal. Next, for a specified region of interest within the beats, the equivalent time points of each beat are grouped together to create ensembles of samples, examples of which are shown at 1002 and 1004 in FIG. 10. A Fourier Transform or Fast Fourier Transform (FFT) of each ensemble is taken to view the frequency behavior of the beats. Other techniques for transforming time domain data to frequency domain data may be used. FIG. 10 only shows two regions of interest 1002 and 1004 for which frequency domain analysis is performed. However, it is possible to have many alternative and/or additional regions of interest. For example, if each beat is made up of 200 samples, there can be 200 regions of interest (one for each time sample) that are analyzed. Then, the region that produces the maximum magnitude of alternans can be considered to be the region of interest used for further analysis.

Returning to FIG. 9, at step 906, the frequency content at 0.5 cycles/beat is determined, based on the frequency domain data. At step 908, myocardial mechanical stability is monitored based on the frequency content at 0.5 cycles/beat. What is unique about step 908 is that the frequency of interest is 0.5 cycles/beat, even though the alternans pattern repeats every N beats, where N is at least 3 (i.e., always greater than 2). The reason the frequency content of interest is 0.5 cycles/beat, in this embodiment, is because only 2 out of the N beats are being analyzed.

Figure 11:
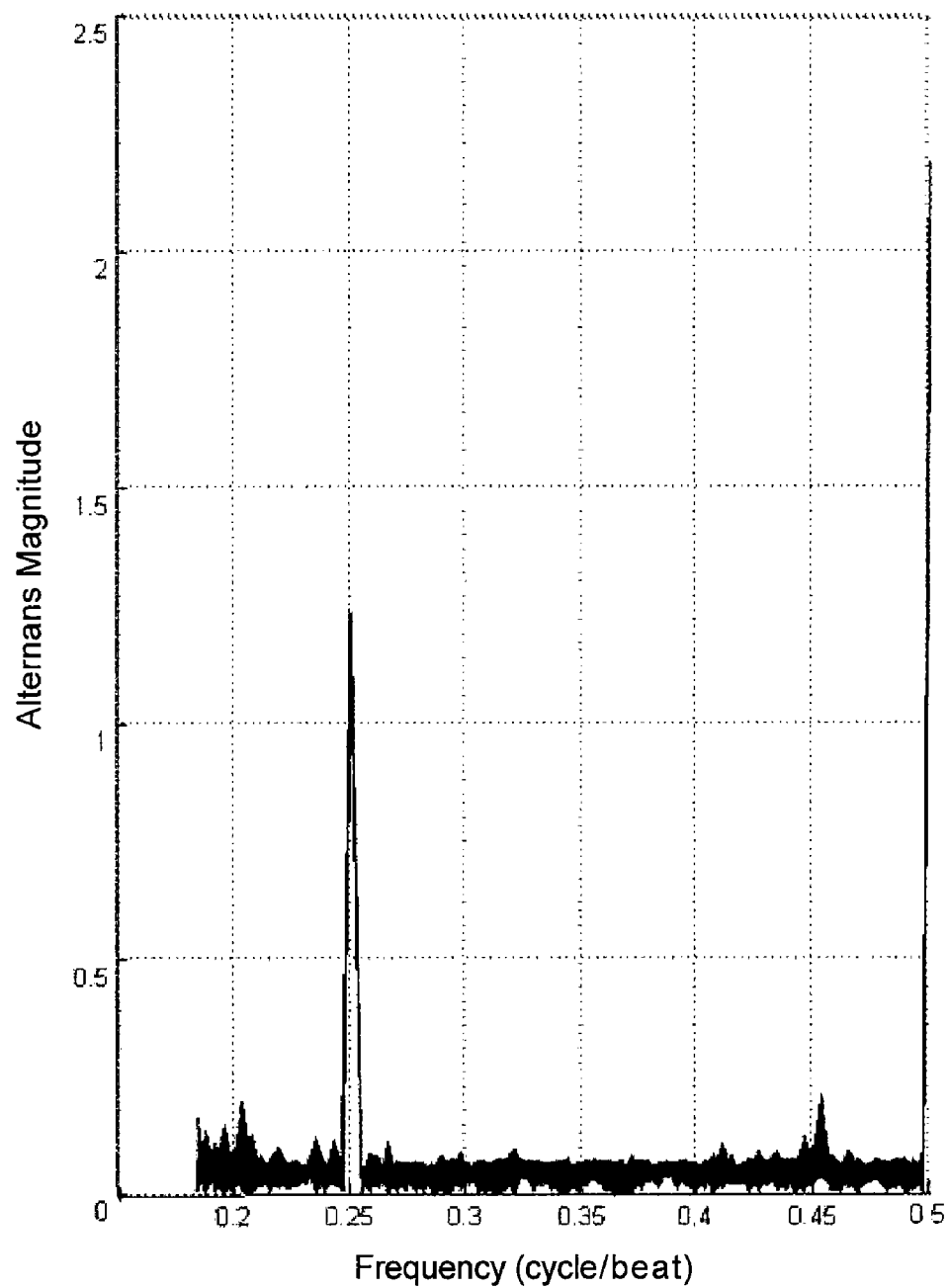
FIG. 11 is an exemplary alternans magnitude versus frequency graph for a patient paced using a patterned pacing sequence that repeats every 4 beats, where the frequency of interest is 0.25 cycles/beat.
Figure 12:
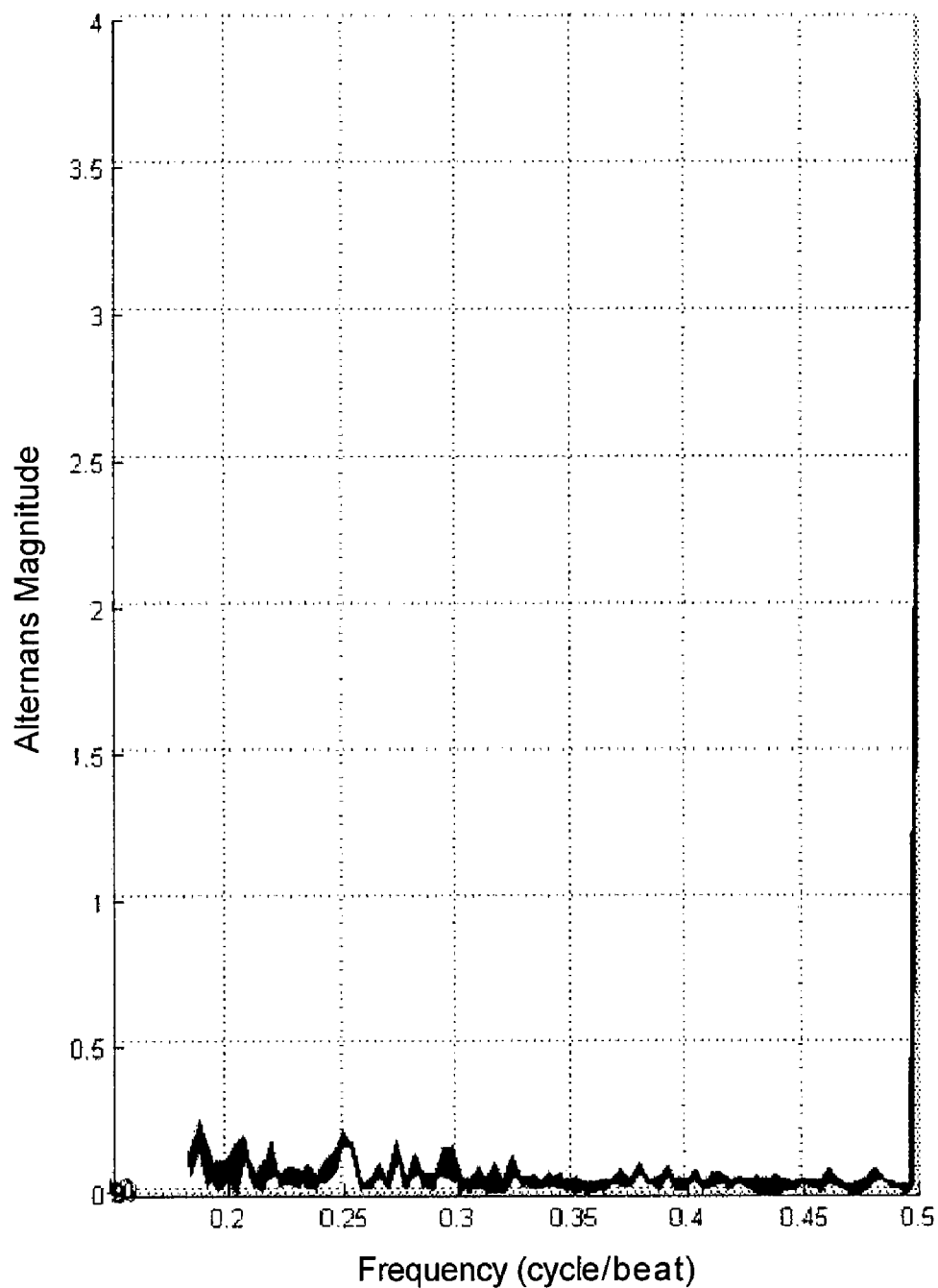
FIG. 12 is an exemplary alternans magnitude versus frequency graph produced starting with the same time domain data used to produce FIG. 11, but using the embodiment of the present invention described with reference to FIG. 9, with the frequency of interest being 0.5 cycles/beat.

The benefits of the frequency domain embodiments of the present invention can be appreciated from the graphs of FIGS. 11 and 12. FIG. 11 is an exemplary alternans magnitude versus frequency graph for a patient that is pacing using a patterned pacing sequence that repeats every 4 beats. Using prior art techniques, it is expected that the frequency of interest is 0.25 (i.e., 1/4 cycles/beat). As can be seen from FIG. 11, the alternans magnitude at 0.25 cycles/beat is about 1.25. It can also be seen that there is an alternans magnitude of about 2.2 at 0.5 cycles/beat.

FIG. 12 is an exemplary alternans magnitude versus frequency graph that was produced starting with the same time domain data used to produce FIG. 11, but using the embodiment of the present invention described with reference to FIG. 9. More specifically, from each 4 beat set (i.e., from each beat pattern ABCD), the first 2 beats (i.e., the AB beats) were selected at step 902 to produce sub-sets of 2 beats each ($A_1B_1$, $A_2B_2 \ldots A_{250}B_{250}$), and then the resulting time domain data was transformed to the frequency domain. In this embodiment of the present invention the frequency of interest is 0.5 cycles/beat, as was described above. As can be seen from FIG. 12, the magnitude at 0.5 cycles/beat is about 3.75, which is three times the 1.25 magnitude at the 0.25 cycles/beat frequency of interest in FIG. 11. The alternans magnitude of 3.75 at 0.5 cycles/beat in FIG. 12 is also more than 50% greater than the alternans magnitude of 2.2 at 0.5 cycles/beat in FIG. 11. Thus, it can be seen from the graphs of FIGS. 11 and 12 that it is more likely that alternans will be detected above noise using the frequency domain embodiments of the present invention described with reference to FIG. 9.

A decision as to whether mechanical alternans are present can be made, e.g., by comparing a peak alternans magnitude to a constant threshold, or a threshold that changes with the noise level. For example, the threshold can be set at a multiple (e.g., 3 times) the mean noise level, where it can be assumed that magnitudes at frequencies prior to the frequencies of interest are noise. For example, if the frequency of interest is 0.5 cycles/beat, it can be assumed that all magnitude of alternans prior to 0.45 cycles/beat are noise.

In a specific embodiment, magnitudes of alternans are tracked over time to thereby track how a patients myocardial mechanical stability changes over time. For example, a patient may be paced for a period of time, once per day (or week, or month or other period) using the same patterned pacing sequence, and a magnitude of alternans can be determined at 0.5 cycles/beat each time. If over time the magnitudes of alternans increase, it can be determined that the patient's myocardial mechanical stability is worsening. If over time the magnitudes of alternans decrease, it can be determined that the patient's myocardial mechanical stability is improving.

Specific embodiments of the present invention are also directed to performing the frequency domain analysis described with reference to FIG. 9, where a patient's heart is not paced.

Responses to Detection of Mechanical Alternans

If an embodiment of the present invention is used to determine that mechanical alternans are present, it can be indicative of heightened risk of heart failure. The ICD 10 may be programmed to respond in a variety of ways.

More specifically, one or more response can be triggered at step 312 (of FIG. 3) if mechanical alternans are determined to be present. In accordance with an embodiment of the present invention, information related to the mechanical alternans can be stored. This can include, for example, storing amplitude, slope, timing, and/or duration information relating to the alternans. Such information can be continually, or from time to time, automatically uploaded to an external device (e.g., 102). Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

As mentioned above, mechanical alternans are a known predictor of heart failure. Accordingly, in an embodiment, a patient is alerted (e.g., using alert 118) when alternans are detected. Such an alert could be a vibratory or auditory alert that originates from within the implantable device 10. Alternatively, the implantable device 10 may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing.

Additionally or alternatively, the patient can be instructed to take medication when alerted. In still another embodiment, a physician or other person (e.g., a caregiver, guardian or relative of the patient) is alerted whenever the presence of mechanical alternans is detected.

In further embodiments, therapy can be triggered in response to detecting the presence of mechanical alternans. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate drug therapy. In still another embodiment, the implanted device, if appropriately equipped, can deliver appropriate resynchronization therapy. These are just a few examples of the types of responses that can be performed upon detection of mechanical alternans. One of ordinary skill in the art would understand from the above description that other response are also possible, while still being within the spirit and scope of the present invention.

In further embodiments, changes in myocardial mechanical stability are tracked, as described above, and one or more of the above described responses occur if the mechanical instability of the myocardium exceeds a corresponding threshold, or mechanical stability of the myocardium falls below a corresponding threshold.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for monitoring myocardial mechanical stability, comprising:
   (a) obtaining a signal that is indicative of mechanical functioning of a patient's heart for a plurality of consecutive beats;
   (b) determining a metric of the signal for each of the plurality of consecutive beats;
   (c) dividing the plurality of consecutive beats into a plurality of sets of N consecutive beats, wherein N is an integer that is at least 2;
   (d) determining, for each of the plurality of sets of N consecutive beats, one or more pairwise combination of the metrics for consecutive pairs of beats;
   (e) cumulative averaging or cumulative summing corresponding pairwise combinations determined for the plurality of sets of N consecutive beats to thereby produce a plurality of cumulative values; and
   (f) monitoring myocardial mechanical stability based on the cumulative values.

2. The method of claim 1, further comprising pacing the patient's heart for a period of time using a patterned pacing sequence that repeats every N beats; and wherein the signal obtained at step (a) is indicative of mechanical functioning of the patient's heart for a plurality of consecutive beats while the patient's heart is being paced using the patterned pacing sequence that repeats every N beats.

3. The method of claim 1, wherein N is an integer that is at least 3.

4. The method of claim 1, wherein step (f) comprises determining, based on the cumulative values, whether mechanical alternans are present.

5. The method of claim 4, wherein:
   step (e) comprises cumulative averaging corresponding pairwise differences determined for the plurality of sets of N consecutive beats to thereby produce the plurality of cumulative values; and
   step (f) comprises determining that mechanical alternans are present when the cumulative values exceed a specified threshold.

6. The method of claim 4, wherein:
   step (e) comprises cumulative summing corresponding pairwise differences determined for the plurality of sets of N consecutive beats to thereby produce the plurality of cumulative values; and
   step (f) comprises determining that mechanical alternans are present when a slope of the cumulative values exceeds a specified slope threshold.

7. The method of claim 1, wherein step (f) comprises tracking changes in myocardial mechanical stability as steps (a) through (g) are repeated over time.

8. The method of claim 1, further comprising bounding the pairwise combinations determined at step (d) prior to the cumulative averaging or cumulative summing performed at step (e).

9. The method of claim 1, further comprising:
   detecting disruptive beats, if they exist, based on the cumulative values determined at step (e); and
   if one or more disruptive beats are detected, compensating for the disruptive beats, and performing steps (c), (d) and (e) again before monitoring myocardial mechanical stability at step (f).

10. The method of claim 9, wherein:
    step (d) comprises cumulative averaging corresponding pairwise differences determined for the plurality of sets of N consecutive beats to thereby produce the plurality of cumulative values; and
    the detecting disruptive beats step comprises detecting a disruptive beat if the cumulative values continually stay within a range and then suddenly go outside the range and continually stay within a further range.

11. The method of claim 9, wherein:
    step (d) comprises cumulative summing corresponding pairwise differences determined for the plurality of sets of N consecutive beats to thereby produce the plurality of cumulative values; and
    the detecting disruptive beats step comprises detecting a disruptive beat if the cumulative values continually increase and then suddenly continually decrease.

12. The method of claim 1, wherein step (a) comprises obtaining a signal selected from the group consisting of:
    a signal is representative of ventricular pressure obtained from a pressure transducer within a ventricle;
    a signal representative of contraction strength obtained from an accelerometer;
    a signal representative of blood flow rate obtained from a blood flow transducer;
    a signal representative of heart rate sounds obtained from a microphone or an accelerometer that responds to acoustic vibrations transmitted through body fluids;
    a signal representative of blood volume obtained using an impedance measuring circuit;
    a signal representative of pulse pressure obtained using a photo-plethysmography sensor; and
    a signal representative of venous oxygen saturation obtained using an SVO2 sensor.

13. An implantable system for monitoring myocardial mechanical stability, comprising:
    one or more sensor configured to obtain a signal that is indicative of mechanical functioning of the patient's heart for a plurality of consecutive beats;
    a measuring means configured to determine a metric of the signal for each of the plurality of consecutive beats; and
    a controller configured to
      divide the plurality of consecutive beats into a plurality of sets of N consecutive beats;
      determine, for each of the plurality of sets of N consecutive beats, one or more pairwise combination of the metrics for consecutive pairs of beats;
      cumulative average or cumulative sum corresponding pairwise combinations determined for the plurality of sets of N consecutive beats to thereby produce a plurality of cumulative values; and
      monitor myocardial mechanical stability based on the cumulative values.

14. The system of claim 13, further comprising one or more pulse generator configured to pace a patient's heart for a period of time using a patterned pacing sequence that repeats every N beats, where N is an integer that is at least 2; and wherein the one or more sensor obtains the signal that is indicative of mechanical functioning of the patient's heart for a plurality of consecutive beats while the patient's heart is being paced using the patterned pacing sequence that repeats every N beats.

15. The system of claim 13, wherein N is an integer that is at least 3.

16. The implantable system of claim 13, wherein the one or more sensor is selected from the group consisting of:
- a pressure transducer configured to be placed within a ventricle to obtain a signal representative of ventricular pressure;
- an accelerometer configured to obtain a signal representative of contraction strength;
- a blood flow transducer configured to obtain a signal representative of blood flow rate;
- a microphone configured to obtain a signal representative of heart rate sounds;
- an accelerometer, that responds to acoustic vibrations transmitted through body fluids, configured to obtain a signal representative of heart rate sounds;
- an impedance measuring circuit configured to obtain a signal representative of blood volume;
- a photo-plethysmography sensor configured to obtain a signal representative of pulse pressure; and
- an SVO2 sensor configured to obtain a signal representative of venous oxygen saturation.

* * * * *

UNITED STATES PATENT AND TRADEMARK OFFICE
CERTIFICATE OF CORRECTION

PATENT NO.       : 7,620,448 B1                      Page 1 of 1
APPLICATION NO. : 11/421915
DATED            : November 17, 2009
INVENTOR(S)      : Farazi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this

Twenty-sixth Day of October, 2010

David J. Kappos
*Director of the United States Patent and Trademark Office*